United States Patent [19]

Schellenberger

[11] Patent Number: 6,156,509

[45] Date of Patent: Dec. 5, 2000

[54] METHOD OF INCREASING EFFICIENCY OF DIRECTED EVOLUTION OF A GENE USING PHAGEMID

[75] Inventor: Volker Schellenberger, Palo Alto, Calif.

[73] Assignee: Genencor International, Inc., Rochester, N.Y.

[21] Appl. No.: 08/968,627

[22] Filed: Nov. 12, 1997

[51] Int. Cl.[7] .................................................. C12Q 1/68
[52] U.S. Cl. ........................ 435/6; 435/183; 435/235.1; 435/441; 435/446; 530/350
[58] Field of Search .............................. 435/6, 441, 446, 435/183, 235.1; 530/350

[56] References Cited

U.S. PATENT DOCUMENTS

| | | | |
|---|---|---|---|
| 4,980,288 | 12/1990 | Bryan et al. | 435/222 |
| 5,521,077 | 5/1996 | Chaitan et al. | 435/441 |
| 5,844,094 | 12/1998 | Hudron et al. | 530/387.3 |

FOREIGN PATENT DOCUMENTS

WO 97/20078   6/1997   WIPO .

OTHER PUBLICATIONS

Bennett et al., "Rapid evolution in response to high–temperature selection," *Nature*, vol. 346, pp. 79–81 (1990).

Coia et al., "Use of Mutator Cells as a Means for Increasing Production Levels of a Recombinant Antibody Directed Against Hepatitis B," *Gene*, vol. 201, pp. 203–209 (1997).

Cox et al., "Structure and coding properties of a dominant *Escherichia coli* mutator gene, mutD," *Proc. Natl Acad. Sci. USA*, V. 80 pp. 2295–2299, Apr. 1983.

Degenen et al., "Conditional Mutator Gene in *Escherichia coli*: Aisolation, Mapping, and Effector Studies," *J. Bacteriol*, vol. 117, No. 2, pp. 477–487, (1974).

DiFrancesco et al., "The Interaction of DNA Polymerase III and the Product of the *Escherichia coli* Mutator Gene, MutD★", *The Journal of Biological Chemistry*, vol. 259, pp. 5567–5573 (1984).

Eigen et al., "The Origin of Genetic Information: Viruses as Models," *Gene*, vol. 135, pp. 37–47 (1993).

Forney et al., "Selection of Amidases with Novel Substrate Specifities from Penicillin Amidase of *Escherichia coli*, *Applied and Environmental Microbiology*," vol. 55, No. 10 pp. 2550–2555 (1989).

Greener et al., "XL1–Red: A Highly Efficient Random Mutagenesis Strain," *Strategies in Molecular Biology*, vol. 7, pp. 32–34 (1994).

Harder et al., "A Review Microbial Selection in Continuous Culture," vol. 43, pp. 1–24 (1977).

Horiuchi et al., "A New Conditional Lethal Mutator (dnaQ49) in *Escherichia coli* K12," *Mol. Gen. Genetics*, vol. 163, pp. 277–283 (1978).

Irving et al., "Affinity Maturation of Recombinant Antibodies Using *E. coli* Mutator Cells," *Immunotechnology*, vol. 2, pp. 127–143 (1996).

Liao et al., "Isolation of a Thermostable Enzyme Variant by Cloning and Selection in a Thermophile," *Proc. Natl. Acad. Sci. USA*, vol. 83, pp. 576–580 (Feb. 1986).

Maki et al., *Proc. Natl. Acad. Sci. U.S.A.* vol. 80, pp. 7137–7141 (1983).

Mao et al., "Proliferation of Mutators in A Cell Population," *Journal of Bacteriology*, pp. 417–422 (1997).

Maruyama et al., "A Dominant (mutD5) and a Recessive (dnaQ49) Mutator of *Escherichia coli*.," *Journal of Molecular Biology*, vol. 167, pp. 757–771 (1983).

Maniatis, "Phagemids: Plasmids Containing an Origin of Replication Derived from a Filamentous Bacteriophage," *Single Stranded, Filamentous Bacteriophage Vectors*, chapter 4 pp. 17–25 (1989).

Matsumura et al., "Screening for Thermopstable Mutant of Kanamycin Nucleotidyltransferase by the Use of a Transformation System for a Thermophile, *Bacillus stearothermophilus*," Journal of Biological Chemistry, vol. 260, No. 28, pp. 15298–15303 (1985).

Oliphant et al., "An Efficient Method for Generating Proteins with Altered Enzymatic Properties: Application to B–Lactamase," *Proc. Natl. Acad. Sci. USA*, vol. 86, pp. 9094–9098 (Dec. 1989).

Prudhomme et al., "Nucleotide Sequence of the *Streptococcus pneumoniae* hexB Mismatch Repair Gene: Homology of HexB to MutL. of *Salmonella typhimurium* and to PMS1 of *Saccharomyces cerevisiae*," *J. Bacteriology*, vol. 171 (10), pp. 5332–5338 (1989).

Schaaper, "An *Escherichia coli* dnaE Mutation with Suppressor Activity toward Mutator mutD5," *Journal of Bacteriology*, vol. 174, pp. 1974–1982 (1992).

Schaaper, "Mechanisms of Mutagenesis in the *Escherichia coli* Mutator mutD5: Role of DNA Mismatch Repair," *PNAS*, vol. 85, pp. 8162–8130 (1988).

Snyder et.al, "Molecular genetics of bacteria," *American Society for Microbiology*, Chap. 3: pp. 85–89 (1997).

Taddel et.al, "Role of Mutator Alleles in Adaptive Evolution," *Nature* vol. 387, pp. 700–702 (1997).

Takano et al., "Sstructure and function of dnaQ and mutD mutators of *Escherichia coli*," Mol. Gen. Genet. vol. 205(1), pp. 9–13 (1986).

(List continued on next page.)

*Primary Examiner*—James Ketter
*Attorney, Agent, or Firm*—Christopher L. Stone; Debra J. Glaister; Genencor International, Inc.

[57] ABSTRACT

An improved method of mutating DNA is provided comprising mutating a gene bearing phagemid in a host and infecting the host cell with a suitable helper phage to initiate packaging of the DNA into a phagemid. The packaged phagemid is then used to infect a second host cell. The method facilitates more efficient screening for genetic diversity. Also, the gene of interest is mutated and separable from the host cell which undergoes the mutational event reducing false positive results or other artifacts of general mutation techniques.

15 Claims, 1 Drawing Sheet

OTHER PUBLICATIONS

Trobner et.al, "Selection Against Hypermutability in *Escherichia coli* During Long Term Evolution," *Genetics* vol. 198, pp. 177–178 (1984).

McClary, J. et al., "Efficient Site–Directed in vitro Mutagenensis Using Phagemid Vectors," *Bio Techniques*, vol. 7, No. 3, pp. 282–289 (1989).

Philippon, A. et al., "Extended–Spectrum β–Lactamases," *Antimicobial Agents and Chemotherapy*, vol. 33, No. 8, pp. 1131–1136 (1989).

Shafikani, S. et al., "Generation of Large Libraries of Random Mutants in *Bacillus subtilis* by PCR–Based Plasmid Multimerization," *Bio Techniques*, vol. 23, No. 2, pp. 304–310 (1997).

Stemmer, W.P.C., "Rapid evolution of a protein in vitro by DNA shuffling," *Nature*, vol. 370, pp. 389–391 (1994).

International Search Report for PCT/US98/23278.

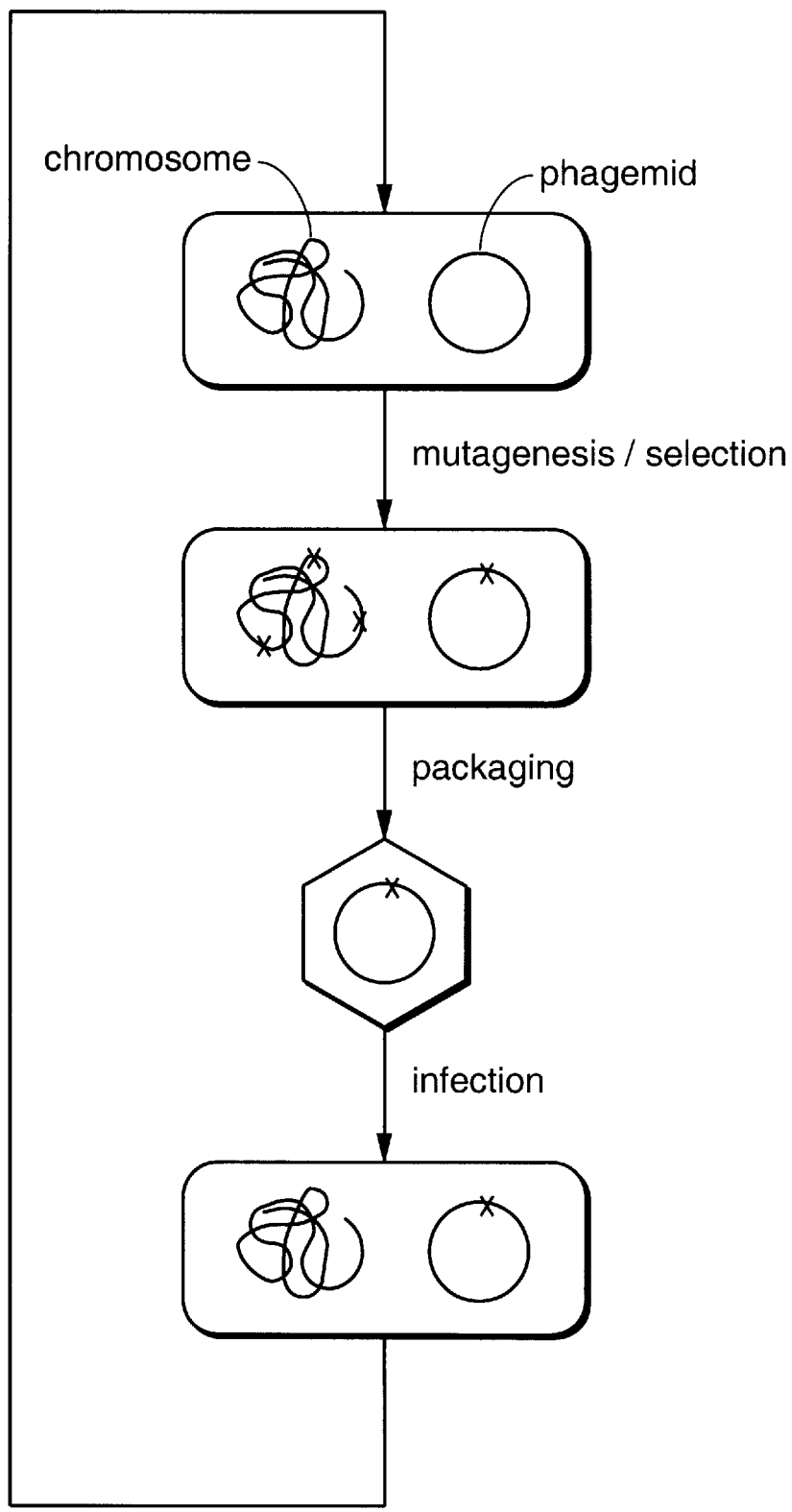
FIG._1

METHOD OF INCREASING EFFICIENCY OF DIRECTED EVOLUTION OF A GENE USING PHAGEMID

BACKGROUND OF THE INVENTION

1. Field of the Invention

The present invention is directed to improved methods for producing mutant proteins. More specifically, the present invention is directed to methods for producing mutant proteins in vivo utilizing phagemids to isolate mutations away from the chromosome or other DNA of the microorganism in which the DNA has been mutated.

2. State of the Art

A number of methods have been utilized to produce useful mutations in proteins of interest. For example, one method widely used comprises chemical mutagens to treat DNA either in vitro or in vivo. Such methods have commonly utilized chemicals such as nitrosoguanidine, hydroxylamine and/or ultraviolet light to generate the mutations. Such methods, however, can be less desirable because of the uncontrolled nature of the mutations and can often be less than random due to the presence of certain "hot spots" within the DNA. Moreover, only certain types of mutations will result, e.g., transversions or transitions, depending on the chemical used.

Polymerase chain reaction has been used to introduce random mutations in genes which have no selectable phenotype. This in vitro method exploits the inherent infidelity of the Taq DNA polymerase during the reaction whereby varying the conditions can cause the PCR process to produce random mutations. Problems with this technique are caused by the need to reclone the gene of interest into a vector after the reaction and also by the need to conduct individual reactions to guarantee independent mutations due to clonal expansion during amplification. As a result, the method becomes quite time consuming and expensive with a resultant small number of random mutants.

Mutator strains facilitating in vivo mutagenesis are an alternative method to introduce random mutations into a gene. Strains of *E. coli* that carry mutations in one of the DNA repair pathways have been described which have a higher random mutation rate than that of typical wild type strains (see, e.g., Miller, J., "A Short Course In Bacterial Genetics," *Cold Spring Harbor Laboratory Press*, 1992, pp.193–211). As reported by Degenen and Cox (*J. Bacteriol.*, 1974, Vol. 117, No. 2, pp.477–487), an *E. coli* strain carrying a mutD5 allele demonstrates from 100 to 10,000 times the mutation rate of its wild type parent. Greener et al., "Strategies In Molecular Biology," 1994, Vol. 7, pp.32–34, disclosed mutator strain with a mutation rate of one base per 2000 nucleotides. Thus, propagation of a plasmid in a mutator strain will generate mutations in the plasmid and, presumably, in the gene of interest.

Recently, vectors have been developed which combine desirable features of both plasmids and filamentous bacteriophages. As described in Sambrook et al., "Molecular Cloning: A Laboratory Manual," *Cold Spring Harbor Press* (1989), in their simplest form, these vectors are plasmids with a ColE1 origin of replication and a selectable marker for antibiotic resistance that carry in addition a copy of the major intergenic region of a filamentous bacteriophage. This intergenic region contains all of the sequences required in cis for initiation and termination of viral DNA synthesis and for morphogenesis of bacteriophage particles. Essentially, segments of foreign DNA cloned in these vectors can be propogated as plasmids in the conventional way. When cells harboring these plasmids are infected with a suitable filamentous bacteriophage, the mode of replication of the plasmid changes under the influence of the gene II product coded by the incoming virus. This gene II protein interacts with the intergenic region carried in the plasmid and initiates rolling-circle replication to generate copies of one strand of the plasmid DNA which will be nicked, circularized, and eventually packaged into progeny bacteriophage particles. In the prior art, the single-stranded DNA purified from these particles have been used as a template for sequencing, for oligonucleotide-directed mutagenesis, and for synthesis of strand-specific probes.

Phagemids are desirable cloning vectors for several reasons, most notably that they provide characteristics, such as high stability and yields of double stranded DNA, that are characteristic of conventional plasmids, they circumvent the tedious and time consuming process of subcloning DNA fragments from plasmids to filamentous bacteriophage vectors, and they are sufficiently small that segments of foreign DNA up to 10 kb in length can be obtained in single stranded form.

Despite the knowledge in the art related to mutating DNA and producing resultant valuable mutants, there is a need in the art to easily produce discrete mutations which effect only effect a desired gene of interest, without effecting the host organism.

SUMMARY OF THE INVENTION

It Is an object of the invention to provide for a more efficient method of producing gene specific mutations.

It is a further object of the invention to provide for a method of producing a mutant gene which is easily packaged and removed from the host cell.

It is yet a further object of the invention to provide for a method of producing a mutant gene through random mutagenesis and simply and efficiently transferring that gene to a host organism which was not subject to such random mutagenesis, thus ensuring that mutations are localized in the gene of interest.

It is yet a further object of the invention to provide for a method of packaging a gene which has been mutagenized in vivo and killing the cell in which the gene was mutagenized.

According to the present invention, a method of preparing a mutant gene is provided comprising the steps of: (a) preparing a DNA consisting of a phagemid comprising a gene of interest; (b) transforming a host cell with the phagemid; (c) subjecting the host cell to a mutational event to produce a mutation in said DNA in said phagemid; (d) infecting the host cell with a suitable helper phage to initiate packaging of the DNA into a phagemid; and (e) infecting a second host cell with the resultant mixture of phage particles.

In a particularly preferred embodiment, the method according to the invention is an iterative method wherein steps (c) through (e) are repeated one or more times preferably under conditions which enrich cells harboring a phagemid with favourable mutations. Preferably, helper phage is present during each of steps (c) through (e), which steps are repeated at least once.

In yet another embodiment, the mutant gene is expressed in a suitable host cell to produce a mutant protein. In a composition embodiment of the invention, a protein encoded by a mutant gene prepared according to the invention is provided.

In yet a further preferred embodiment, helper phage is present during each infection step.

In another embodiment the gene of interest is cloned directly into a phage, preferably a lysogenic phage. Upon infection the phage DNA including the gene of interest will be incorporated into the genome of the host where it can be subjected to mutagenesis and the host population can be subjected to selection or screening for improved mutants of the gene of interest. Subsequently, lysis and phagemid packaging can be induced to separate mutations in the gene of interest (true positives) from mutations in the host chromosome (false positives).

Thus, an advantage of the present method is that cells carrying the phagemid can be more efficiently screened where efforts are made to generate genetic diversity. For example, when the resulting mutant population is subjected to screening or selection to identify or enrich clones with desired phenotype, the selected clones can have mutations in the phagemid (true positives) or in the chromosome (false positives). The present method eliminates the false positives sue to chromosome mutations.

Another advantage of the invention is that the gene of interest is mutated and separable from the host cell which undergoes the mutational event. Accordingly, it is possible to screen for mutations in the gene of interest without unknown bias or selection error due to mutations within the chromosome of the host cell which effect the results of a screening or selection step confirming the presence of desirable mutations.

BRIEF DESCRIPTION OF THE DRAWING

FIG. 1 illustrates in schematic form the directed evolution of a plasmid using a phagemid protocol.

DETAILED DESCRIPTION OF THE INVENTION

"Phagemid" means vectors known in the art which combine features of both plasmids and bacteriophages. Generally, phagemids are characterized by two stages in their replication cycle, the first bearing resemblance to traditional plasmids in that a selectable marker and a gene of interest are present on, for example, a circularized or linear strand of DNA. In this form, phagemids can be introduced and propagated as plasmids in the conventional manner, i.e., transformation into a host cell and subsequent replication and amplification of the plasmid DNA material. In their second stage, the cell containing the phagemid DNA of the first stage is infected with a helper phage which, due to the presence of genetic information from bacteriophage in the phagemid DNA, causes the phagemid DNA to change its mode of replication to rolling-circle replication of single stranded copies of plasmid DNA which are nicked, circularized and eventually packaged into progeny bacteriophage particles. Upon packaging the cells release the phagemid particles which can then reinfect other cells.

Among the useful phagemids for the present invention are those well known in the art. For example, the literature provides useful examples of phagemids characterized by their inclusion of well known plasmid components combined with well known phage intergenic regions such as e.g., the phagemid which combines pEMBL plasmid and f1 phage intergenic region described in (Dente et al., *Nucleic Acids Res.*, Vol. 11, p. 1645 (1983)), the phagemid that combines pBR322 plasmid with the M13 intergenic region (Zagursky et al., *Gene*, Vol. 27, p. 183 (1984)), the phagemid which combines pRSA101 plasmid and M13 phage intergenic region (Levinson et al., *Mol. Appl. Genet.*, Vol. 2, p. 507 (1984)), the phagemid which combines the pUC118/119 plasmid with the M13 intergenic region (Vieria et al., *Meth. Enzymol.*, Vol. 153, p. 3 (1987)) and the phagemid which combines the pBluescript plasmid with the f1 phage intergenic region (Short et al., *Nucleic Acids Res.*, Vol. 16, p. 7583 (1988)).

"Host cell" means a cell which has the capacity to act as a host and expression vehicle for a recombinant DNA vector according to the present invention. In a preferred embodiment according to the present invention, "host cell" means the cells of *Escherichia coli, Bacillus spp., Aspergillus spp., Trichoderma spp., Humicola spp., Fusarium spp.*, or any other microbial, plant or mammalian host cell system generally available in the art. Where the host cell is to be subjected to a mutational event to mutate the gene of interest, it is preferred that the host cell is a mutator strain.

"Mutational event" means an event which causes a mutation in a particular piece of DNA. Methods of subjecting a particular gene or DNA fragment to a mutational event are known in the art and include, e.g., chemical treatment using such known mutating agents as nitrosoguanidine, sodium bisulfite, nitrous acid, hydrazine, formic acid, 5-bromouracil, 2-aminopurine, acridine, proflavine, acriflavine, quinacrine, hydroxylamine and/or ethidium bromide, ultraviolet light, X-rays, low fidelity polymerase chain reaction using the Taq polmerase, oligonucleotide-directed mutagenesis or other site specific means of altering a DNA sequence, altering sequences within restriction endonuclease sites, inserting an oligonucleotide linker randomly into a plasmid or other art recognized and accepted means of introducing a subsitution, deletion or addition of a DNA base or bases within a given strand of DNA or its replication products. In an especially preferred method of carrying out the invention, a mutator strain is used. Mutator strains are specific strains which have been modified to carry mutations in one or more of their DNA repair pathways. Accordingly, their rate of spontaneous random mutation is higher than that of a wild type parent of the strain. In one embodiment, the mutator strain is *E. coli* and the strain carries the muts or mutD allele. Such strains may have mutation rates that are 50–100 times higher, or greater, than that of a wild type parent. The XL1-Red strain of *E. coli* is a particularly useful strain for this purpose, see e.g., Greener et al., Strategies in Molecular Biology, 1994, Vol.7, pp.32–34.

In an exemplary embodiment, the cloning vector employed is a phagemid and the host cell is an *E. coli* mutator strain. The gene of interest is inserted into the appropriate location of the phagemid using standard techniques (see e.g., Sambrook, supra). The phagemid can then be transformed into the host cell. Methods for transforming a mutant gene encoding phagemid DNA into a suitable recipient host cell are known to those of skill in the art and typically include the use of calcium chloride or other agents, such as divalent cations and DMSO. DNA can also be introduced into bacterial cells by electroporation.

At this point, the mutator strain will inherently introduce mutations throughout the host cell and the phagemid, although it is additionally possible to subject the cell to an external mutational event as well. Subsequently, upon addition of helper phage to the mixture containing the host cell which contains the phagemid, single stranded DNA is packaged and extruded from the cell in the form of a transducing phage in a manner common to phage vectors. Clonal amplification of the resultant mutant encoding nucleotide sequences carried by phagemids can be accomplished by optionally separating the phagemid from the original host cells and host cell fragments, or ensuring that the host cells are generally non-competent, and reinfecting another batch of suitable host cells with the phagemid suspension. The mutation-packaging-reinfection sequence may be repeated as often as desired until the gene has been subjected to a desirable level of mutational activity. At this point, the mutant gene carrying phagemid particles may be propagated into a suitable host cell or manipulated according to known methods to induce expression protein encoded by the mutant gene.

A preferred method is to combine the generation of mutations and the selection of favourable mutations into one process. For that purpose the gene of interest is expressed in the mutator strain and variants which exhibit increased activity of the gene are being enriched by selection or screening.

Infection, or transfection, of host cells with helper phage or phagemid particles in the phage state may be accomplished according to well known techniques in the art (see, e.g., Sambrook and Russel et al., Gene, 1986, Vol. 45, pp. 333–338).

The helper phage which find utility in the claimed methods may be any phage which can be used in combination with the specific cloning phagemid used which is able to produce an infective transducing phagemid particle. For example, in one embodiment, where the cloning vector may be a phagemid, the helper phage may be Ml3 or f1.

By following the teachings of the invention provided herein, the mutant gene bearing phagemid is separated from the host cell which was subjected to the mutational event and which, accordingly, may bear unwanted supplementary mutations within its genomic DNA. These unwanted supplementary mutations within the host cell may have the effect of masking or mimicking improvements caused by mutations in the gene of interest which would interfere with subsequent selection or screening. Furthermore, mutations in the host may decrease the viability or impair other necessary traits of the host.

The following examples are offered for illustrative purposes and are not intended to limit the scope of the present invention in any way, the proper scope being delimited by the claims.

EXAMPLE

Evolution of TEM-1 β-lactamase

*E. coli* XL1-blue was transformed with pBG66 (Palzkill et. al., Proteins, vol. 14, pp. 29–44, (1992)) using standard procedures.

1. The cells were grown in LB (carb) and infected with helper phage, VCS-M13 (Stratagene) which resulted in the packaging of pBG66.

2. *E. coli* KH1366 (Hfr, dnaQ45) was obtained from the *E. coli* genetic stock center. The strain is Hfr which makes it infectable by M13 and it carries the dnaQ45 mutation which results in an elevated mutation frequency Horiuchi et al., *Molec. Gen. Genet.*, 1978, Vol. 163, pp.277–283.

3. KH1366 was infected with pBG66 (from 1) and grown in LB(carb) and a glycerol stock was prepared.

4. KH1366/pBG66 was grown in 50 ml LB(20 mg/l amp) at 37° C. to saturation. 50 μl of the culture were transferred into 50 ml of fresh medium and grown overnight. The resulting culture was infected with VCS-M13 to package and was called G003.

5. KH1366 were grown at 26° C. in LB to a density of about $10^8$ cells/ml.

6. 4 ml LB, 0.5 ml KH1366 (step 5) and 0.5 ml packaged plasmid were mixed and incubated for 15 min at 37° C. without shaking.

7. Several cultures of 49 ml LB containing various amounts of cefotaxime, ctx, were inoculated with 1 ml of the culture (step 6) and grown for 20 h at 37° C.

8. The culture with the highest ctx concentration that showed a cell density$>6\times10^7$ cells/ml was diluted to $6\times10^7$ cells/ml and grown 1 h at 37° C. 2 ml of that culture was infected with 11 μl VCS-M13 ($10^{10}$ pfu/ml) and grown for 2.5–3 h to allow packaging.

9. The culture was heated to 65° C. for 15 min to kill all cells and centrifuged for 2 min at 14 krpm. The resulting supernatant was used to initiate the next round of evolution starting at step 5.

The process was repeated during 6 rounds. The phagemids from each round were used to infect XL1-blue and the minimal inhibitory concentration, MIC, for ctx was determined as described in Petrosino et al., *J. Bacteriol.*, 1996, Vol. 178, pp. 1821–1828.

Table 1 gives the observed MICs and the concentrations of ctx of the cultures from which the populations were obtained.

TABLE 1

| Phagemid | MIC (mg/l) | ctx during selection (mg/l) |
|---|---|---|
| pBG66 | 0.02 | |
| G003 | 0.04 | 0 |
| G300 | 3.8 | .1 |
| G301 | 3.8 | .8 |
| G302 | 7.7 | 6.4 |
| G303 | 15 | 6.4 |
| G304 | 31 | 6.4 |
| G305 | 31 | 51.2 |

Resistance to ctx that is conferred by the phagemid increased dramatically during the process and the final population was about 1500 times more resistant to ctx than the starting clone, pBG66.

Two clones were isolated from population G305 and the TEM-1 gene was sequenced. Both clones carried the same 4 mutations. One of the mutations was silent. The other three lead to amino acid changes E104K, G238S, and T265M. All three mutations have been previously found in the clinical isolate TEM-4 (Philippon et al., *Antimicrob. Agents Chemother.*, 1989, Vol. 33, pp.1131–1136). Mutations El 04K and G238S have also been identified previously by gene shuffling (Stemmer, *Nature*, 1994, Vol. 370, pp.389–391). The isolate clones had no mutations in the promoter which indicates that the improvements in the MICs are mainly due to an increase in the specific activity of β-lactamase for ctx and not due to increased levels of expression.

I claim:

1. A method of preparing a mutant gene comprising the steps of:
   (a) subjecting a first host cell transformed with a phagemid comprising a gene of interest to a mutational event wherein said subjecting produces a host cell population comprising a mutant of said gene;
   (b) subjecting said host cell population to selection for mutant of said gene; and
   (c) infecting said host cell population with a suitable helper phage to initiate packaging of said phagemid comprising said mutant gene.

2. The method according to claim 1, wherein said helper phage is present during steps (a) and (b).

3. The method according to claim 1, wherein the gene of interest has been cloned into a lysogenic phagemid.

4. The method of claim 1 further comprising isolating said mutant gene.

5. The method according to claim 1, wherein said gene of interest comprises DNA encoding an enzyme or a protein having pharmaceutical utility.

6. The method according to claim 1, wherein said phagemid further comprises a selectable marker.

7. The method according to claim 6, wherein said selectable marker comprises DNA encoding a protein which confers antibiotic resistance.

8. The method according to claim 3, wherein said lysogenic phagemid is integrated into the genome of said host cell.

9. The method according to claim 4, wherein said isolated mutant gene is expressed in a host cell to produce a mutant protein.

10. The method of claim 1 wherein said first host cell is a mutator strain and said subjecting comprises growing said strain.

11. The method of claim 1 wherein step (a) and step (b) are combined into one process.

12. The method of claim 1 further comprising the step of (d) obtaining phagemid particles resulting from step (c) and infecting a second host cell with said particles.

13. The method according to claim 12, wherein said steps (a) through (d) are repeated one or more times.

14. The method of claim 12 wherein said second host cell is a mutator strain.

15. A method of preparing a mutant gene comprising the steps of:
   (a) preparing a phagemid comprising a gene of interest;
   (b) transforming a first host cell with said phagemid;
   (c) subjecting said first host cell to a mutational event to produce a host cell population comprising a mutant of said gene and subjecting said host cell population to selection for a mutant of said gene;
   (d) infecting said first host cell population with a suitable helper phage to initiate packaging of said phagemid;
   (e) infecting a second host cell with the resultant mixture of phage particles.

* * * * *